United States Patent
Murthy et al.

(10) Patent No.: US 6,600,044 B2
(45) Date of Patent: Jul. 29, 2003

(54) PROCESS FOR RECOVERY OF THE DESIRED CIS-1,3-OXATHIOLANE NUCLEOSIDES FROM THEIR UNDESIRED TRANS-ISOMERS

(75) Inventors: K. S. Keshava Murthy, Brantford (CA); Gurijala V. Reddy, Brantford (CA); Zhi-xian Wang, Brantford (CA); Chandrawansha B. W. Senanayake, Brantford (CA)

(73) Assignee: Brantford Chemicals Inc., Brantford ( * ) Notice: Subject to any disclaimer, the term of this patent is extended or adjusted under 35 U.S.C. 154(b) by 0 days.

(21) Appl. No.: 09/881,705

(22) Filed: Jun. 18, 2001

(65) Prior Publication Data

US 2003/0013880 A1 Jan. 16, 2003

(51) Int. Cl.$^7$ .................... C07D 411/04; C07D 473/16; C07D 473/18
(52) U.S. Cl. .............. 544/264; 544/265; 544/266; 544/272; 544/276; 544/277; 544/298; 544/301; 544/302; 544/311; 544/312; 544/313; 544/314; 544/316; 544/317; 544/318; 544/319; 544/320; 544/322; 544/323; 544/327; 544/332; 544/334; 544/335
(58) Field of Search ................ 544/264, 265, 544/266, 272, 276, 277, 298, 301, 302, 311, 312, 313, 314, 316, 317, 318, 319, 320, 322, 323, 327, 332, 334, 335

(56) References Cited

U.S. PATENT DOCUMENTS

| | | | |
|---|---|---|---|
| 5,047,407 A | 9/1991 | Belleau et al. | 514/274 |
| 5,486,520 A | 1/1996 | Belleau, et al. | 514/274 |
| 5,539,116 A | 7/1996 | Liotta et al. | 544/317 |
| 6,228,860 B1 * | 5/2001 | Mansour et al. | 514/263.23 |
| 6,380,388 B1 * | 4/2002 | Murthy et al. | 544/317 |

FOREIGN PATENT DOCUMENTS

| | | |
|---|---|---|
| EP | 0 515 157 A1 | 5/1992 |
| EP | 0 517 145 A1 | 6/1992 |
| WO | PCT WO 91/17159 | 11/1991 |
| WO | PCT WO 94/05686 | 3/1994 |
| WO | PCT WO 95/29174 | 11/1995 |
| WO | PCT WO 00/09494 | 2/2000 |
| WO | WO 00/09494 A1 * | 2/2000 |

OTHER PUBLICATIONS

J. Med. Chem. 1993, 36, 181–195.
J. Matulic–Adamic, et. al., in "Sterochemical features of the anomerizations in the 5,6–dihydrothymine nucleoside series" (*J. Chem. Soc. Perkin Trans. 1*, 1988, 2681–2686).
D. Thacker and T. L. V. Ulbricht, in "General Lewis acid catalysis of glycoside anomerization and O→N–glycosyl rearrangement" (*Chem. Commun.* 1967, 122–123).
T.C. Britton et al., in "Process for anomerizing nucleosides" (EP 587364 A1 and B1).
L. S. Jeong, et. al. in "Asymmetric Synthesis and Biological Evaluation of β–L–(2R,5S)–and α–L–(2R, 5R)–1,3–Oxathiolane–Pyrimidine and purine Nucleosides as potential anti–HIV agents" (*J. Med. Chem.* 1993, 36, 181–195).
D. C. Humber, et. al. in "Expeditious preparation of (–)–2'–deoxy–3'–thiacytidine (3TC)" (*Tetrahedron Lett.* 1992, 33, 4625–4628).
*J. Org. Chem.* 1992, 57, 2217–2219.
F. Seela and H.D. Winkler, in "2–Amino–7–β–D–arabinofuranosyl–4–methoxy–7H–pyrrolo[2,3–d]pyrimidine: a facile preparation and anomerization of a 7–deazapurine nucleoside" (*Carbohydrate Research*, 1983, 118, 29–53).
J. Cadet, *Tetrahedron Lett.*, 1974, 867–870.
J. Cadet and R. Teoule, in "Nucleic acid hydrolysis. I. Isomerization and anomerization of pyrimidic deoxyribonucleosides in an acidic medium" (*J. Am. Chem. Soc.*, 1974, 96, 6517–6519).
R.T. Walker et.al., in "A mild procedure for the anomerization of 2'–deoxynucleosides" (*Tetrahedron Lett.*, 1993, 34, 6779–6782).
L. N. Beigelman et. al., in "Epimerization during the acetolysis of 3–O–acetyl–5–O–benzoyl–1,2–O–isopropylidene–3–C–methyl–α–D–ribofuranose. Synthesis of 3'–C–methylnucleosides with the β–D–ribo–and α–D–arabino configurations" (*Carbohydr. Res.* 1988, 181, 77–88).
Charron, et al. in "Recycling of an undesired trans–[1,3]–oxathiolane nucleoside analogue by epimerization" (82$^{nd}$ Canadian Institute for Chemistry Conference, Organic Chemistry Abstract #530, May 30–Jun. 2, 1999, Toronto, Canada).
V. W. Armstrong, et.al., in "The base catalysed anomerisation of β –5–formyluridine; crystal and molecular structure of α–formyluridine" (*Nucleic Acid Res.*, 1976, 3, 1791–1810).

(List continued on next page.)

*Primary Examiner*—Richard L. Raymond
*Assistant Examiner*—Thomas McKenzie
(74) *Attorney, Agent, or Firm*—Ivor M. Hughes, Barrister & Solicitor, Patent & Trademark Agents

(57) ABSTRACT

A process for the preparation of 1,3-oxathiolane nucleoside analogues in predominantly the cis-form, from mixture of cis-/trans-1,3-oxathiolane nucleosides or their protected derivatives thereof, comprising:

(i) treatment of the cis-/trans-1,3-oxathiolane nucleosides (or protected derivatives thereof) with a pyrimidine base (or it derivatives thereof) and an acid, (ii) adding a suitable acid to the obtained cis-/trans-mixture of isomers, (iii) selective crystallization of the desired cis-isomer salt from a solvent or combination of solvents, and (iv) treatment of the predominantly cis-isomer salt with a suitable base to offer the free 1,3-oxathiolane nucleosides, and thereafter optionally repeating steps (i) to (iv) inclusive.

17 Claims, No Drawings

OTHER PUBLICATIONS

T. Ueda, et. al., in "Synthesis of 5–alkyl–and 5–acyl–uridines via 6–mercaptouridine (nucleosides and nucleotides. XVII)" (*Heterocycles*, 1977, 8, 427–432).

H. Vorbruggen et. al. in "Nucleoside Synthesis, XXII. Nucleoside Synthesis with Trimethylsilyl Triflate and Perchlorate as Catalysts" (*Chem. Ber.* 1981, 114, 1234–1255).

T. Yamaguchi and M. Saneyoshi in "Synthetic Nucleosides and Nucleotides. XXI. On the synthesis and biological evaluations of 2'–deoxy–α –D–ribofuranosy nucleosides and nucleotides" (*Chem. Pharm. Bull.*, 1984, 32, 1441–1450).

M. Miyaki et. al. in "N→N Alkyl and glycosyl migrations of purines and pyrimidines. IV. Trans–Glycosylation from pyrimidines to purines. (A novel synthetic method of purine nucleosides and nucleotides)" (*Chem. Pharm. Bull.*, 1970, 2459–2468).

M. Imazawa and F. Eckstein in "Synthesis of 3'–azido–2', 3'–dideoxyribofuranosylpurines" (*J. Org. Chem.* 1978, 43, 3044–3048).

B. Shimizu and M. Miyaki in "Transglycosylation from pryimidines to purines" (*Tetrahedron Lett.*, 1968, 855–859).

T. Azuma, et. al. in "Chemical transglycosylation of octosyl acid" (*Tetrahedron Lett.*, 1976, 1687–1690).

T. Azuma, et. al. in "Transglycosylation: an improved method for tansglycosylation from pyrimidines to purines" (*Chem. Pharm. Bull.* 1977, 25, 3347–3353).

M. Imazawa and F. Eckstein in "Facile Synthesis of 2'–Amino–2'–deoxyribofuranosyl Purines" (*J. Org. Chem.* 1979, 44, 2039–2041).

J. Kiss, et. al. in "Sterospecific synthesis of the anticancer agent 5'–deoxy–5–fluorouridine (5–DFUR) and its 5'–deuterated derivatives" (*Helv. Chim. Acta* 1982, 65, 1522–37).

A. V. Azhayev et. al. in "Aminonucleosides and their derivatives; XIII. Synthesis of Benzimidazole azidonucleosides" (*Synthesis*, 1985, 410–411).

S. L. Beaucage, et. al., in "Synthesis and physicochemical properties of alternating α,β–oligodeoxyribonucleotides with alternating (3'→3')–and (5'→5')–internucleotidic phosphodiester linkages" (*J. Org. Chem.* 1995, 60, 1520–1530).

K. Pongracz and S. M. Gryaznov, in "α–Oligodexyribonucleotide N3'→N5' phosphoramidates: synthesis and duplex formation" (*Nucleic Acids Research*, 1998, 26, 1099–1106).

M.–C. Liu, et. al. in "Synthesis and Biological Evaluation of 1,3–Oxathiolane 5–Azapyrimidine, 6–Azapyrimidine, and Fluorosubstituted 3–Deazapyrimidine Nucleosides" (*Nucleosides, Nucleotides & Nucleic Acids*, 2000, 19, 603–618).

D. A. Carson and D. Bruce Wasson in "Synthesis of 2',3'–dideoxylnucleosides by enzymatic trans–glycosylation" (*Biochem. Biophys. Res. Commun.* 1988, 155, 829–834).

* cited by examiner

PROCESS FOR RECOVERY OF THE DESIRED CIS-1,3-OXATHIOLANE NUCLEOSIDES FROM THEIR UNDESIRED TRANS-ISOMERS

BACKGROUND OF THE INVENTION

The present invention relates to commercial processes for the production of antiviral cis-1,3-oxathiolane and 1,3-dioxolane nucleoside analogues, some of which include, but are not limited to cis-(−)-4-amino-1-[2-(hydroxymethyl)-1,3-oxathiolan-5-yl]-2(1H)-pyrimidinone (1, Lamivudine, 3TC, BCH-189) and its 5-fluoro analogue, cis-(−)-4-amino-5-fluoro-1-[2-(hydroxymethyl)-1,3-oxathiolan-5-yl]-2(1H)-pyrimidinone (2, Emtricitabine, (−)-FTC)). In particular, the present invention relates to a new and efficient process for converting the undesired trans-1,3-oxathiolane and 1,3-dioxolane nucleoside isomers to the desired cis-1,3-oxathiolane and 1,3-dioxolane nucleoside isomers by a method of anomerization/transglycosylation, and a highly efficient method of separating the anomeric mixture of 1,3-oxathiolane nucleoside analogues to their single anomers.

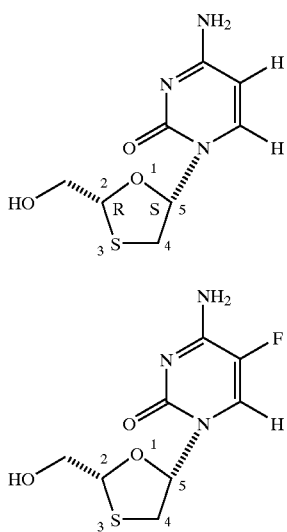

2,5-Disubstituted 1,3-oxathiolanes with pyrimidines or purine bases possess potent activities against the replication of the human immunodeficiency viruses (HIV) and hepatitis B virus (HBV). 3TC (1) has been approved as an antiviral for the treatment of HIV and HBV infection and its 5-fluoro analogue, (−)-FTC (2) is currently in advanced clinical trials for the same infections and shown promise as selective agent.

Generally speaking, there are two chiral centers in most of 1,3-oxathiolane and 1,3-dioxolane nucleosides and these nucleosides can exist in two distinct stereoisomeric forms, known as cis (β) and trans (α) diastereomers. Each cis- or trans-diastereomer is further composed of a pair of stereoisomers, known as enantiomers, and one of which displays high activity against viral infection. For many nucleoside analogues, including 3TC and FTC, the antiviral activity is significantly more pronounced in one of two possible enantiomeric forms of cis-diastereomer. In the case of 3TC and FTC, the levorotatory, or (−), enantiomer is the major contributor to the desired antiviral activity, as is disclosed in the following: U.S. Pat. No. 5,047,407; PCT WO 91/17159; U.S. Pat. No. 5,486,520; U.S. Pat. No. 5,539,116; J. Org. Chem. 1992, 57, 2217–2219; J. Med. Chem. 1993, 36, 181–195. Therefore, it would be very advantageous if these antiviral nucleoside analogues, especially 3TC and (−)-FTC, could be produced industrially in a straight forward and in a highly diastereoselective and enatioselective manner. Processes which would allow efficient preparation of pharmacologically desirable diastereomerically enriched cis-isomer, or, separation of cis/trans mixtures to provide diastereomerically enriched cis-isomer, or, efficient conversion into diastereomerically enriched cis-isomer from a mixture of trans-diastereomer and cis-diastereomer, are highly desirable.

Generally speaking there are two main strategies that have been used in the prior art for obtaining the desired enantiomer from the coupling of an oxathiolane derivative and a base. In the first strategy, the oxathiolane derivative is racemic and it is coupled to a base using various known coupling procedures giving only the racemic cis-isomer or a mixture of isomers (cis/trans) which is separated using known diastereomeric techniques to give the desired racemic cis-isomer. The racemic cis-isomer is resolved using enzymatic or chiral chromatography techniques (see for example EP 517145, PCT WO 00/09494). In the second strategy, single enantiomer or enantiomerically enriched 1,3-oxathiolane derivatives are coupled to a base to give a mixture of cis/trans-diastereomers, which can be separated using known diastereomeric techniques (see for example PCT W095/29174, PCT WO 00/09494).

The first strategy is not attractive because the resolution is performed at the end of the process and guarantees that 50% of the product would be the unwanted enantiomer which could not be easily converted to the desired enantiomer since two chiral centers would have to be inverted.

An advantage of the second strategy is that the resolution at the C-2 position of 1,3-oxathiolane derivatives occurs early in the process. Although an anomeric mixture may result where up to 50% of the product could be the unwanted trans-isomer, the possibility of converting the trans-isomer to the cis-isomer via anomerization/trans-glycosilation stands a much better chance of success than what would be needed in the first strategy since only one chiral center needs to be inverted. The second strategy could give a theoretical yield of 100% after the coupling step.

Nucleoside anomerization employing protic acids or Lewis acids has been applied to a wide variety of nucleosides and includes for example: 2M HCl, see F. Seela and H. D. Winkler, in "2-Amino-7-β-D-arabinofuranosyl-4-methoxy-7H-pyrrolo[2,3-d]pyrimidine: a facile preparation and anomerization of a 7-deazapurine nucleoside" (Carbohydrate Research, 1983, 118, 29–53); 1M HBr, see J. Cadet, Tetrahedron Lett., 1974, 867–870; NaI/HOAc, see J. Matulic-Adamic, et. al., in "Stereochemical features of the anomerizations in the 5,6-dihydrothymine nucleoside series" (J. Chem. Soc. Perkin Trans. 1, 1988, 2681–2686); 2N HClO$_4$, see J. Cadet and R. Teoule, in "Nucleic acid hydrolysis. I. Isomerization and anomerization of pyrimidic deoxyribonucleosides in an acidic medium" (J. Am. Chem. Soc., 1974, 96, 6517–6519); Ac$_2$O/H$_2$SO$_4$, see R. T. Walker et. al., in "A mild procedure for the anomerization of 2'-deoxynucleosides" (Tetrahedron Lett., 1993, 34, 6779–6782) and R. T. Walker et. al., in "Anomerisation process" (PCT WO 94/05686); Lewis acids, see D. Thacker and T. L. V. Ulbricht, in "General Lewis acid catalysis of glycoside anomerization and O→N-glycosyl rearrangement" (Chem. Commun. 1967, 122–123); AcOH, see L. N.

Beigelman et. al., in "Epimerization during the acetolysis of 3-O-acetyl-5-O-benzoyl-1,2-O-isopropylidene-3-C-methyl-α-D-ribofuranose. Synthesis of 3'-C-methylnucleosides with the β-D-ribo-and α-D-arabino configurations" (*Carbohydr. Res.* 1988, 181, 77–88). This type of anomerization involves acid catalyzed sugar ring opening, forming a carbon cation at the anomeric carbon and cyclization to form the anomeric mixture of the nucleosides. This method is not suitable for 1,3-oxathiolane nucleoside analogues since the C-2 position of 1,3-oxathiolane ring could be epimerized under the reaction condition, which has been confirmed by Charron, et al. in "Recycling of an undesired trans-[1,3]-oxathiolane nucleoside analogue by epimerization" (82$^{nd}$ Canadian Institute for Chemistry Conference, Organic Chemistry Abstract #530, May 30–Jun. 2, 1999, Toronto, Canada).

Base mediated anomerization has also been reported such as in, for example, 1:1 4N aqueous NaOH/Methanol; see V. W. Armstrong, et. al., in "The base catalysed anomerisation of β-5-formyluridine; crystal and molecular structure of α-formyluridine" (*Nucleic Acid Res.*, 1976, 3, 1791–1810); 2N aqueous NaOH, T. Ueda, et. al., in "Synthesis of 5-alkyl- and 5-acyl-uridines via 6-mercaptouridine (nucleosides and nucleotides. XVII)" (*Heterocycles*, 1977, 8, 427–432); anhydrous LiOH or KOH/MeOH, T. C. Britton et al., in "Process for anomerizing nucleosides" (EP 587364). This method may not be suitable for 1,3-oxathiolane systems since the 2-hydroxymethyl branch could also be epimerized. This comes about because the methine (C-2 position of 1,3-oxathiolane ring) proton on the oxo,thio acetal system is acidic, can be abstracted and thereby can lead to epimerization.

Nucleoside trans-glycosylation has been accomplished by the treatment of protected nucleoside with a base in the presence of a Lewis acid. The method has been applied for preparing anomeric mixture of the nucleosides, for example, H. Vorbruggen et. al. in "Nucleoside Synthesis, XXII. Nucleoside Synthesis with Trimethylsilyl Triflate and Perchlorate as Catalysts" (*Chem. Ber.* 1981, 114, 1234–1255) disclosed that a silylated α-pyrimidinedione ribofuranosyl nucleoside was treated with TMS-triflate in acetonitrile to afford an α-/β-mixture (67/27) of that nucleoside. T. Yamaguchi and M. Saneyoshi in "Synthetic Nucleosides and Nucleotides. XXI. On the synthesis and biological evaluations of 2'-deoxy-α-D-ribofuranosy nucleosides and nucleotides" (*Chem. Pharm. Bull.*, 1984, 32, 1441–1450) described that the fully acylated 2'-deoxycytidine was reacted with TMS-triflate and bis(trimethylsilyl)-acetamide (BSA) in dry acetonitrile at 70° C. to give a mixture of cis-/trans-anomers. The reaction was believed to occur in two steps as an inter-molecular reaction. First, the trimethylsilylated base is released from the nucleoside and then the liberated active sugar carbonium cation at anomeric carbon position is attacked again by the nucleophilic center (for instance, N1-position of the pyrimidine base). This reaction can also be used for preparing a new nucleoside by employing a new base. M. Miyaki et. al. in "N→N Alkyl and glycosyl migrations of purines and pyrimidines. IV. Trans-Glycosylation from pyrimidines to purines. (A novel synthetic method of purine nucleosides and nucleotides)" (*Chem. Pharm. Bull.*, 1970, 2459–2468) described that trans-glycosylation from pyrimidines to purines catalyzed by Lewis acid such as HgBr$_2$ and SnCl$_4$. M. Imazawa and F. Eckstein in "Synthesis of 3'-azido-2',3'-dideoxyribofuranosylpurines" (*J. Org. Chem.* 1978, 43, 3044–3048) described that the trans-glycosylation reaction of 3'-azido-2',3'-deoxy-5'-O-acetylthymidine with silylated N6-octanoyladenine using trimethylsilyl trifluoromethanesulfonate as a catalyst afforded a mixture of α and β anomers of 3'-azido-2',3'-dideoxyadenosine. Such examples also can be found in the following articles: B. Shimizu and M. Miyaki in "Transglycosylation from pyrimidines to purines" (*Tetrahedron Lett.*, 1968, 855–859); T. Azuma, et. al. in "Chemical transglycosylation of octosyl acid" (*Tetrahedron Lett.*, 1976, 1687–1690); T. Azuma, et. al. in "Transglycosylation: an improved method for tansglycosylation from pyrimidines to purines" (*Chem. Pharm. Bull.* 1977, 25, 3347–3353); M. Imazawa and F. Eckstein in "Facile Synthesis of 2'-Amino-2'-deoxyribofuranosyl Purines" (*J. Org. Chem.* 1979, 44, 2039–2041); J. Kiss, et. al. in "Stereospecific synthesis of the anticancer agent 5'-deoxy-5-fluorouridine (5-DFUR) and its 5'-deuterated derivatives" (*Helv. Chim. Acta* 1982, 65, 1522–37); A. V. Azhayev et. al. in "Aminonucleosides and their derivatives; XIII. Synthesis of Benzimidazole azidonucleosides" (*Synthesis*, 1985, 410–411); S. L. Beaucage, et. al., in "Synthesis and physicochemical properties of alternating α,β-oligodeoxyribonucleotides with alternating (3'→3')- and (5'→5')-internucleotidic phosphodiester linkages" (*J. Org. Chem.* 1995, 60, 1520–1530); K. Pongracz and S. M. Gryaznov, in "α-Oligodexyribonucleotide N3'→N5' phosphoramidates: synthesis and duplex formation" (*Nucleic Acids Research*, 1998, 26, 1099–1106); M.-C. Liu, et. al. in "Synthesis and Biological Evaluation of 1,3-Oxathiolane 5-Azapyrimidine, 6-Azapyrimidine, and Fluorosubstituted 3-Deazapyrimidine Nucleosides" (*Nucleosides, Nucleotides & Nucleic Acids*, 2000, 19, 603–618).

D. A. Carson and D. Bruce Wasson in "Synthesis of 2',3'-dideoxylnucleosides by enzymatic trans-glycosylation" (*Biochem. Biophys. Res. Commun.* 1988, 155, 829–834) disclosed that 2',3'-dideoxynucleosides could be prepared by enzymatic trans-glycosylation using the trans-N-deoxyribosylase from *Lactobacillus helveticus*.

Although anomerization/epimerization and trans-glycosylation of general nucleosides have been well studied, efficient anomerization and trans-glycosylation reactions for converting pharmacologically undesired trans-1,3-oxathiolane and trans-1,3-dioxolane nucleosides into their pharmacologically desired cis-isomers or cis-/trans-isomers mixture have not been explored.

The current processes for the separation of cis-/trans-isomers of 1,3-oxathiolane and 1,3-dioxolane nucleosides are also limited. They are often separated by physical means e.g. chromatographic method (L. S. Jeong, et. al. in "Asymmetric Synthesis and Biological Evaluation of β-L-(2R,5S)- and α-L-(2R, 5R)-1,3-Oxathiolane-Pyrimidine and purine Nucleosides as potential anti-HIV agents" (*J. Med. Chem.* 1993, 36, 181–195); D. C. Humber, et. al. in "Expeditious preparation of (−)-2'-deoxy-3'-thiacytidine (3TC)" (*Tetrahedron Lett.* 1992, 33, 4625–4628)) or by crystallization method (in "Process for the diastereoselective synthesis of nucleoside analogues" (WO 95/29174), in "Processes for the diastereoselective synthesis of nucleosides" (EP 0 515 157 A1), and in "Method of manufacture of 1,3-oxathiolane nucleosides" (WO 00/09494). These processes started from the nucleosides with chiral auxiliary or the diastereomeric enriched nucleosides mixture). As can be seen, an efficient and straightforward method for separating cis-/trans-isomers mixture of 1,3-oxathiolane and 1,3-dioxolane nucleosides, especially 1:1 cis-/trans-isomers mixture, still need to be developed.

SUMMARY OF THE INVENTION

It is therefore an object of the present invention to provide a commercial process for the conversion of pharmacologically undesired trans-1,3-oxathiolane and 1,3-dioxolane nucleoside analogues into the desired cis-form. In particular, according to one aspect of the invention, a process is provided for increasing the amount of cis-nucleoside isomer of the formula

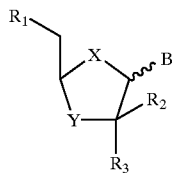

in a mixture of cis-nucleoside and trans-nucleoside isomers, wherein $R_1$ is selected from the group consisting of hydrogen, lower alkyl, fluoro, azide, hydroxy, and OA where A is a lower alkyl, aryl, alkylsilyl, and acyl groups; $R_2$ is selected from the group consisting of hydrogen, azide, lower alkyl, fluoro, hydroxy (provided $R_3$ cannot be fluoro, azide, or hydroxy), and OA where A is as defined above; $R_3$ is selected from the group consisting of hydrogen, azide, lower alkyl, fluoro, hydroxy (provided $R_2$ cannot be fluoro, azide, or hydroxy), and OA where A is as defined above; X and Y are independently selected from the group consisting of oxygen and sulfur; and B is a pyrimidine or purine base, which includes, but is not limited to, 6-alkylpurine and $N^6$-alkylpurines, $N^6$-acylpurines, $N^6$-benzylpurine, 6-halopurine, $N^6$-acetylenic purine, $N^6$-acyl purine, $N^6$-hydroxyalkyl purine, 6-thioalkyl purine, $N^2$-alkylpurines, $N^4$-alkylpyrimidines, $N^4$-acylpyrimidines, 4-halopyrimidines, $N^4$-acetylenic pyrimidines, 4-amino and $N^4$-acyl pyrimidines, 4-hydroxyalkyl pyrimidines, 4-thioalkyl pyrimidines, thymine, cytosine, 6-azapyrimidine, including 6-azacytosine, 2- and/or 4-mercaptopyrimidine, uracil, $C^5$-alkylpyrimidines, $C^5$-benzylpyrimidines, $C^5$-halopyrimidines, $C^5$-vinylpyrimidine, $C^5$-acetylenic pyrimidine, $C^5$-acyl pyrimidine, $C^5$-hydroxyalkyl purine, $C^5$-amidopyrimidine, $C^5$-cyanopyrimidine, $C^5$-nitropyrimidine, $C^5$-aminopyrimidine, $N^2$-alkylpurines, $N^2$-alkyl-6-thiopurines, 5-azauracilyl, triazolopyridinyl, imidazolopyridinyl, pyrrolopyrimidinyl, and pyrazolopyrimidinyl. Functional oxygen and nitrogen groups on the base can be protected as necessary or desired. Suitable protecting groups are well known to those skilled in the art, and include trimethylsilyl, dimethyl-t-hexylsilyl, t-butyldimethylsilyl, and t-butyldiphenylsilyl, trityl, alkyl groups, acyl groups such as acetyl, propionyl and butyryl, methanesulfonyl, and p-toluenesulfonyl. Preferred bases include cytosine, 5-fluorocytosine, uracil, thymine, adenine, guanine, xanthine, 2,6-diaminopurine, 6-aminopurine, 6-chloropurine and 2,6-dichloropurine.

Surprisingly we have discovered a novel process for converting the undesired trans-1,3-oxathiolane and 1,3-dioxolane nucleoside analogues, in their protected or unprotected forms into a mixture of the desired cis- and trans-isomers by trans-glycosylation such as, for example, (i) by treating the undesired trans nucleoside with a suitable acid and a purine or pyrimidine base, or a derivative thereof, or (ii) by treating the undesired trans nucleoside with a suitable silylation reagent (such as BSA which is an anacronym for (bis-trimethyl-silyl) acetamide) and a suitable acid such as a Lewis acid in the presence or in the absence of a nucleoside base, to provide the mixture of cis-/trans-isomers. The mixture of cis-/trans-isomers, if necessary, can be separated such as via the crystallization of them or their organic or inorganic acid salts, for example, according to a procedure we disclose below.

It is also an object of this invention to provide a process for the efficient separation of desired cis-1,3-oxathiolane and 1,3-dioxolane nucleoside analogues of formula (3) from the mixtures of cis-/trans-isomers. In accordance with an aspect of the invention, a process is provided for the separation of the anomeric mixture of 1,3-oxathiolane and 1,3-dioxolane nucleosides, comprising the use of pyrimidine or purine base. Another aspect of the invention also provides a process for separating them in their optically active forms. The anomeric mixture may be, for example, treated with a suitable acid, and the corresponding salts of isomers are separated in their cis- or trans-form in high optical purity and high chemical yield by a method of fractional crystallization. The pharmacologically desired cis-isomer salt is subject to free basing to offer cis-1,3-oxathiolane or 1,3-dioxolane nucleoside. The undesired trans isomers can also be recycled and subjected to anomerization/trans-glycosylation to re-form desired cis-isomers in accordance with aspects of the invention.

DETAILS OF EMBODIMENTS OF THE INVENTION.

In aspects of the present invention, the undesired 1,3-oxathiolane nucleosides trans-isomers (compound 4), in their protected or unprotected form, may be subjected to anomerization/trans-glycosylation in the presence of acids and a pyrimidine or purine base in a single solvent or solvent mixture, to give the desired cis-1,3-oxathiolane nucleoside analogues or the mixture of cis- and trans-isomers (5).

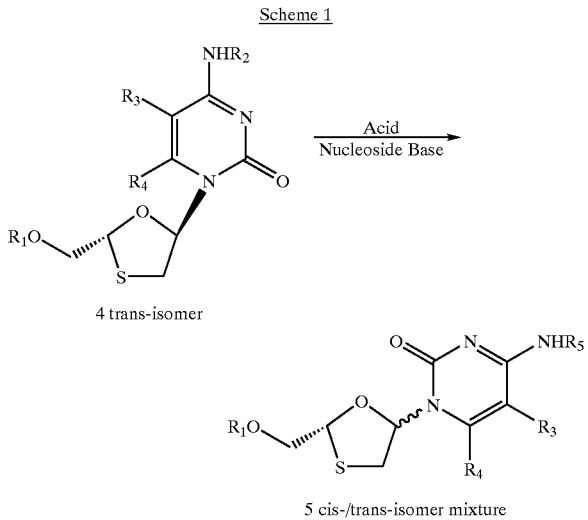

Scheme 1 depicts such a process, wherein $R^1$, $R^2$, $R^5$ are independently selected from the group consisting of hydrogen, alkyl, alkylsilyl, aryl and acyl groups and $R^3$ and $R^4$ are independently selected from the group consisting of hydrogen, bromine, chlorine, fluorine, iodine, low alkyl, aryl, amino and hydroxyl groups.

The nucleosides, which are used as the starting material, can be single trans-isomers or trans-/cis-isomer mixtures, for example, predominantly as the trans-isomer.

Examples of the preferable 1,3-oxathiolane nucleosides produced are, for instance, cis-(−)-4-amino-1-[2-(hydroxymethyl)-1,3-oxathiolan-5-yl]-2(1H)-pyrimidinone (1, 3TC), cis-(−)-4-amino-5-fluoro-1-[2-(hydroxymethyl)-1,3-oxathiolan-5-yl]-2(1H)-pyrimidinone (2, FTC), and the like.

The acids which can be used for this process, include, but are not limited to, chlorotrimethylsilane, bromotrimethylsilane, iodotrimethylsilane, trimethylsilyl trifluoromethanesulfonate, trimethylsilyl trifluoroacetate, triethylsilyl trifluoromethanesulfonate, t-butyldimethylsilyl chloride, t-butyldimethylsilyl trifluoromethanesulfonate, methyl trifluoromethanesulfonate, boron trichloride, boron trifluoride, boron tribromide, boron triiodide, boron trifluoroacetate, trifluoroacetic acid, methanesulfonic acid, p-toluenesulfonic acid. The preferable acids are, for instance, iodotrimethylsilane, trimethylsilyl trifluoromethanesulfonate, p-toluenesulfonic acid, and the like.

The amount of the acid can range from 0.05 to 5 moles per mole of the nucleoside. The preferable amount of the acid is from 1.0 to 2.0 moles per mole of the nucleoside.

The pyrimidine or purine bases can be used as is or in their protected forms. Suitable protecting groups are well known to those skilled in the art, and include trimethylsilyl, dimethyl-t-hexylsilyl, t-butyldimethylsilyl, and t-butyldiphenylsilyl, trityl, alkyl groups, acyl groups such as acetyl, propionyl and butyryl, methanesulfonyl, and p-toluenesulfonyl. Preferred bases include cytosine, 5-fluorocytosine, and the like.

The amount of the pyrimidine bases can range from 0 to 5 moles per mole of the nucleoside. The preferable amount is from 0.5 to 1.5 moles per mole of the nucleoside.

Examples of the preferable solvents for trans-glycosylation/anomerization are, for instance, toluene, benzene, xylenes, dichloromethane, dichloroethanes, chloroform, acetonitrile, tetrahydrofuran, ethers, 1,4-dioxane, etc., and their mixtures.

The reaction temperature preferably ranges from −25° C. to 150° C. The preferable reaction temperature is from 0 to 50° C.

The overall chemical yield of the trans-glycosylation/anomerization generally ranges from 30% to 99%.

The ratio of the product of cis-/trans-nucleosides mixture ranges from 1:5 (cis/trans) to 1:0(cis/trans) after anomerization. The most common ratio is from 1:2 (cis/trans) to 2:1(cis/trans).

After trans-glycosylation/anomerization, the protected nucleosides mixture is subjected to de-protection by using known procedures if necessary, for instance, base mediated deacylation, and the like. The cis-/trans-nucleosides mixture can be separated by the fractional crystallization of their salts of an inorganic or organic acid, by employing the following procedure.

As shown in scheme 2, the mixture of cis-/trans-isomers of 1,3-oxathiolane nucleoside analogues (6) is treated with inorganic or organic acids in a single solvent or solvent mixture; the corresponding salts of isomers are separated in high optical purity by fractional crystallization. The desired cis-nucleoside salts (7) are isolated in high optical purity and high chemical yields. These salts are converted into their corresponding free base form by treatment with organic or inorganic bases in a single solvent or a solvent mixture in high chemical yields. The undesired trans-nucleoside salts (8) are also isolated in high optical purity and chemical yield and they can be recycled by following the process we disclosed in the present invention.

Scheme 2

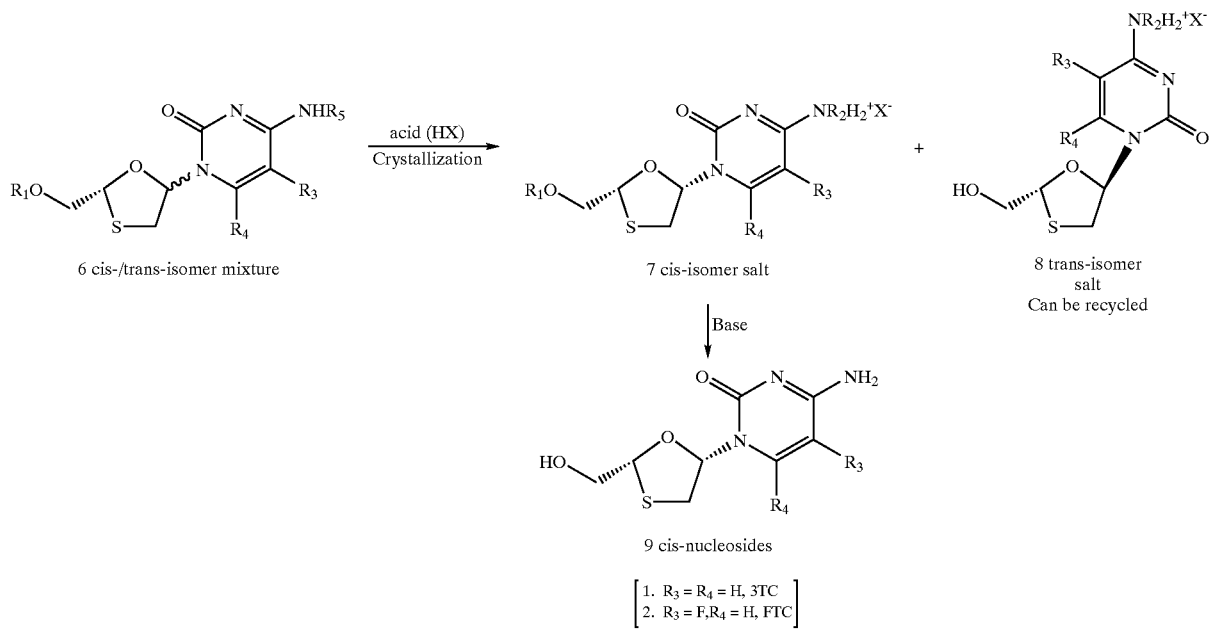

wherein $R^1$ may be hydrogen, low alkyl, aryl, alkylsilyl, and acyl groups. $R^2$ may be hydrogen, alkyl, aryl, and alkylsilyl acyl groups. $R^3$ and $R^4$ are independently selected from the group consisting of hydrogen, bromine, chlorine, fluorine, iodine, low alkyl, aryl, amino and hydroxyl groups.

Examples of the preferable 1,3-oxathiolane nucleosides produced are, for instance, cis-(−)-4-amino-1-[2-(hydroxymethyl)-1,3-oxathiolan-5-yl]-2(1H)-pyrimidinone (1, 3TC), cis-(−)-4-amino-5-fluoro-1-[2-(hydroxymethyl)-1,3-oxathiolan-5-yl]-2(1H)-pyrimidinone (2, FTC), and the like.

Examples of the inorganic and organic acids which can be used for the salt formation and separation, include, but are not limited to, methanesulfonic acid, hydrochloric acid, hydrobromic acid, sulfuric acid, benzenesulfonic acid, p-toluenesulfonic acid. The preferable acids are methanesulfonic acid, hydrochloric acid, and the like. The process may use a single acid, or use a combination of several acids.

The amount of the acid can range from 0.5 to 5 moles per mole of the nucleoside. The preferable amount of the acid is from 1.0 mole to 1.5 moles per mole of the nucleoside.

Examples of the preferable solvents for fractional crystallization can be protic or aprotic such as methanol, ethanol, propanols, butanols, ethers, ethyl acetate, water, etc., and their mixtures.

The overall chemical yield for separating the two isomers ranges from 30 to 99%.

Examples of the preferable organic or inorganic bases for free basing step are, for instance, sodium carbonate, sodium bicarbonate, potassium carbonate, potassium bicarbonate, sodium hydroxide, potassium hydroxide, triethylamine, ammonium hydroxide, ammonia, basic resins, and the like. The process may use a single base, or use a combination of several bases.

Examples of the preferable solvents for the free basing step are, for instance, methanol, ethanol, propanols, butanols, ethers, ethyl acetate, water, etc., and their mixtures.

Thus, in accordance with an aspect of the invention, a process is provided for the preparation of 1,3-oxathiolane nucleoside analogues in predominantly the cis-form, from mixture of cis-/trans-1,3-oxathiolane nucleosides or their protected derivatives thereof, comprising:

(i) treatment of the cis-/trans-1,3-oxathiolane nucleosides (or protected derivatives thereof) with a pyrimidine base (or it derivatives thereof) and an acid, (ii) adding a suitable acid to the obtained cis-/trans-mixture of isomers, (iii) selective crystallization of the desired cis-isomer salt from a solvent or combination of solvents, and (iv) treatment of the predominantly cis-isomer salt with a suitable base to offer the free 1,3-oxathiolane nucleosides, and thereafter optionally repeating steps (i) to (iv) inclusive.

According to an aspect of the invention, the 1,3-oxathiolane nucleoside provided may be cis-(−)-4-amino-1-[2-(hydroxymethyl)-1,3-oxathiolan-5-yl]-2(1H)-pyrimidinone (Lamivudine, 3TC).

Further, according to another aspect of the invention, the 1,3-oxathiolane nucleoside produced is cis-(−)-4-amino-5-fluoro-1-[2-(hydroxymethyl)-1,3-oxathiolan-5-yl]-2(1H)-pyrimidinone (Emtricitabine, (−)-FTC).

Further, according to another aspect of the invention, the pyrimidine base is N,O-disilyled cytosine.

Further, according to another aspect of the invention, the pyrimidine base is N,O-disilyled 5-fluoro-cytosine.

Further, according to another aspect of the invention, the acid for anomerization/trans-glycosylation is iodotrimethylsilane or trimethylsilyl trifluoromethanesulfonate.

Further, according to another aspect of the invention, the acid used for salt formation is methanesulfonic acid or hydrochloric acid.

Further, according to another aspect of the invention, the solvent for crystallization is ethanol, methanol, and ethyl acetate.

Further, according to another aspect of the invention, cis-(−)-4-amino-1-[2-(hydroxymethyl)-1,3-oxathiolan-5-yl]-2(1H)-pyrimidinone, mesylate is provided.

Further, according to another aspect of the invention, cis-(−)-Amino-5-fluoro-1-[2-(hydroxymethyl)-1,3-oxathiolan-5-yl]-2(1H)-pyrimidinone, mesylate is provided.

Further, according to another aspect of the invention, a process is provided for the conversion of pharmacologically undesired trans-1,3-oxathiolane and 1,3-dioxolane nucleoside analogues into the desired cis-form thereby increasing the amount of cis-nucleoside isomer of the formula

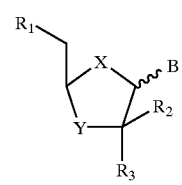

3 in a mixture of cis-nucleoside and trans-nucleoside isomers is provided, wherein $R_1$ is selected from the group consisting of hydrogen, lower alkyl, fluoro, azide, hydroxy, and OA where A is a lower alkyl, aryl, alkylsilyl, and acyl groups; $R_2$ is selected from the group consisting of hydrogen, azide, lower alkyl, fluoro, hydroxy (provided $R_3$ cannot be fluoro, azide, or hydroxy), and OA where A is as defined above; $R_3$ is selected from the group consisting of hydrogen, azide, lower alkyl, fluoro, hydroxy (provided $R_2$ cannot be fluoro, azide, or hydroxy), and OA where A is as defined above; X and Y are independently selected from the group consisting of oxygen and sulfur; and B is a pyrimidine or purine base, which includes, but is not limited to, 6-alkylpurine and $N^6$-alkylpurines, $N^6$-acylpurines, $N^6$-benzylpurine, 6-halopurine, $N^6$-acetylenic purine, $N^6$-acyl purine, $N^6$-hydroxyalkyl purine, 6-thioalkyl purine, $N^2$-alkylpurines, $N^4$-alkylpyrimidines, $N^4$-acylpyrimidines, 4-halopyrimidines, $N^4$-acetylenic pyrimidines, 4-amino and $N^4$-acyl pyrimidines, 4-hydroxyalkyl pyrimidines, 4-thioalkyl pyrimidines, thymine, cytosine, 6-azapyrimidine, including 6-azacytosine, 2- and/or 4-mercaptopyrimidine, uracil, $C^5$-alkylpyrimidines, $C^5$-benzylpyrimidines, $C^5$-halopyrimidines, $C^5$-vinylpyrimidine, $C^5$-acetylenic pyrimidine, $C^5$-acyl pyrimidine, $C^5$-hydroxyalkyl purine, $C^5$-amidopyrimidine, $C^5$-cyanopyrimidine, C5-nitropyrimidine, $C^5$-aminopyrimidine, $N^2$-alkylpurines, $N^2$-alkyl-6-thiopurines, 5-azauracilyl, triazolopyridinyl, imidazolopyridinyl, pyrrolopyrimidinyl, and pyrazolopyrimidinyl and wherein functional oxygen and nitrogen groups on the base can be protected as necessary or desired by suitable protecting groups which may include trimethylsily, dimethyl-t-hexylsilyl, t-butyldimethylsilyl, and t-butyldiphenylsilyl, trityl, alkyl groups, acyl groups such as acetyl, propionyl and butyryl, methanesulfonyl, and p-toluenesulfonyl by trans-glycosilation, (i) by treating the undesired trans nucleoside with a suitable acid and a suitable purine or pyrimidine base, or a derivative thereof, or (ii) by treating the undesired trans nucleoside with a suitable silylation reagent (such as BSA (bis-trimethyl silyl) acetamide) and a suitable acid such as a Lewis acid in the presence or in the absence of a nucleoside base, to provide the mixture of cis-/trans-isomers.

Further, according to another aspect of the invention, the process is carried out by carrying out the process of subparagraph (i) in the immediately preceding paragraph.

Further, according to another aspect of the invention, the process is carried out by carrying out the process of subparagraph (ii) above in the next to the immediately preceding paragraph.

Further, according to another aspect of the invention, the mixture of cis-/trans-isomers can be separated via the crystallization of them or their organic or inorganic acid salts.

Further, according to another aspect of the invention, the pharmacologically desired cis-isomer salt is subject to free basing to offer cis-1,3-oxathiolane or 1,3-dioxolane nucleoside and wherein the undesired trans compounds are optionally recycled and subjected to anomerization/transglycosylation to re-form desired cis-isomers.

Further, according to another aspect of the invention, a process is provided for converting 1,3-oxathiolane nucleosides trans-isomers (compound 4),

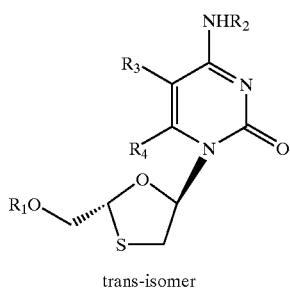

trans-isomer in their protected or unprotected form, the process comprising subjecting the trans-isomers to anomerization/transglycosylation in the presence of acids and a suitable pyrimidine or purine base in a single solvent or solvent mixture, to give the desired cis-1,3-oxathiolane nucleoside analogues or the mixture of cis- and trans-isomers (5)

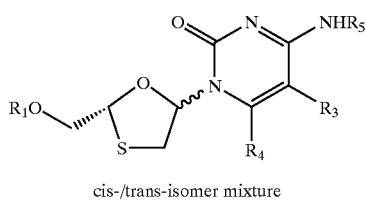

cis-/trans-isomer mixture

Further, according to another aspect of the invention, $R_1$, $R_2$, $R_5$ are independently selected from the group consisting of hydrogen, alkyl, alkylsilyl, aryl and acyl groups. $R_3$ and $R_4$ are independently selected from the group consisting of hydrogen, bromine, chlorine, fluorine, iodine, low alkyl, aryl, amino and hydroxyl groups.

Further, according to another aspect of the invention, the nucleosides, which are used as the starting material, are selected from single trans-isomers or trans-/cis-isomer mixtures predominantly containing the trans-isomer.

Further, according to another aspect of the invention, the 1,3-oxathiolane nucleosides produced are selected from cis-(−)-4-amino-1-[2-(hydroxymethyl)-1,3-oxathiolan-5-yl]-2(1H)-pyrimidinone (1, 3TC), cis-(−)-4-amino-5-fluoro-1-[2-(hydroxymethyl)-1,3-oxathiolan-5-yl]-2(1H)-pyrimidinone (2, FTC), and the like.

Further, according to another aspect of the invention, the acids are selected from chlorotrimethylsilane, bromotrimethylsilane, iodotrimethylsilane, trimethylsilyl trifluoromethanesulfonate, trimethylsilyl trifluoroacetate, triethylsilyl trifluoromethanesulfonate, t-butyldimethylsilyl chloride, t-butyldimethylsilyl trifluoromethanesulfonate, methyl trifluoromethanesulfonate, boron trichloride, boron trifluoride, boron tribromide, boron triiodide, boron trifluoroacetate, trifluoroacetic acid, methanesulfonic acid, p-toluenesulfonic acid.

Further, according to another aspect of the invention, the acids are selected from iodotrimethylsilane, trimethylsilyl trifluoromethanesulfonate, and the like.

Further, according to another aspect of the invention, the amount of the acid ranges from 0.05 to 5 moles per mole of the nucleoside.

Further, according to another aspect of the invention, the amount of the acid is from 1.0 to 2.0 moles per mole of the nucleoside.

Further, according to another aspect of the invention, the pyrimidine or purine bases are selected from pyrimidine and purine bases protected by trimethylsily, dimethyl-t-hexylsilyl, t-butyldimethylsilyl, and t-butyldiphenylsilyl, trityl, alkyl groups, acyl groups such as acetyl, propionyl and butyryl, methanesulfonyl, and p-toluenesulfonyl.

Further, according to another aspect of the invention, the bases are selected from cytosine, 5-fluorocytosine, and the like.

Further, according to another aspect of the invention, the amount of the pyrimidine bases can range from 0 to 5 moles per mole of the nucleoside.

Further, according to another aspect of the invention, the amount of base is from 0.5 to 1.5 moles per mole of the nucleoside.

Further, according to another aspect of the invention, a process is provided comprising treating a mixture of cis-/trans-isomers of 1,3-oxathiolane nucleoside analogues (6)

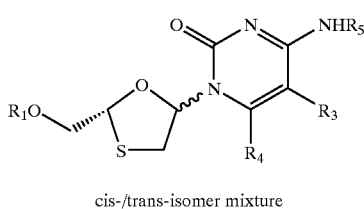

cis-/trans-isomer mixture with inorganic or organic acids in a single solvent or solvent mixture; the corresponding salts of the isomers being thereafter separated in high optical purity by fractional crystallization, the desired cis-nucleoside salts (7)

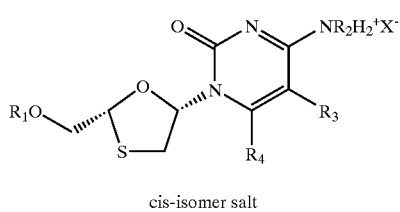

cis-isomer salt being isolated and converted into their corresponding free base form (9) by treatment with organic or inorganic bases in a single solvent or a solvent mixture, the undesired trans-nucleoside salts (8)

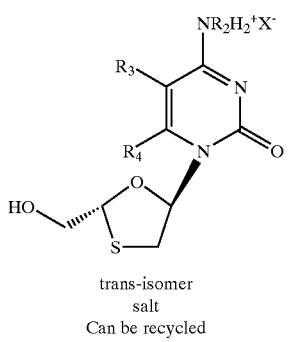

trans-isomer
salt
Can be recycled also being isolated and recycled by repeating the process thereby to produce

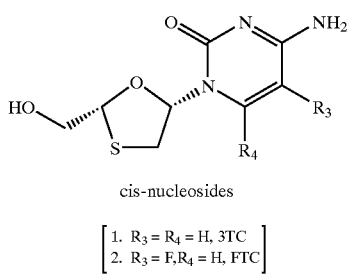

cis-nucleosides $$\begin{bmatrix} 1.\ R_3 = R_4 = H,\ 3TC \\ 2.\ R_3 = F, R_4 = H,\ FTC \end{bmatrix}$$

wherein $R_1$ is selected from hydrogen, low alkyl, aryl, alkylsilyl, and acyl groups, $R_2$ selected from hydrogen, alkyl, aryl, and alkylsilyl groups and $R_3$ and $R_4$ are independently selected from the group consisting of hydrogen, bromine, chlorine, fluorine, iodine, low alkyl, aryl, amino and hydroxyl groups.

Further, according to another aspect of the invention, $R_3=R_4=H$ in compound 9 and compound 9 is 3TC.

Further, according to another aspect of the invention, $R_3$ is F and $R_4$ is H in compound 9 and compound 9 is FTC.

Further, according to another aspect of the invention, the inorganic and organic acids are selected from methanesulfonic acid, hydrochloric acid, hydrobromic acid, sulfuric acid, benzenesulfonic acid, p-toluenesulfonic acid.

Further, according to another aspect of the invention, the acid is selected from methanesulfonic acid, hydrochloric acid, and the like.

Further, according to another aspect of the invention, the amount of the acid can range from 0.5 to 5 moles per mole of the nucleoside.

Further, according to another aspect of the invention, the amount of the acid is from 1.0 mole to 1.5 moles per mole of the nucleoside.

The following non-limiting examples show the process for producing desired cis-1,3-oxathiolane nucleosides from undesired trans-1,3-oxathiolane nucleosides, and the separation of the cis-/trans-mixture of 1,3-oxathiolane nucleosides, via the processes of the present invention.

EXAMPLE 1

Preparation of 4-Butyrylamino-5-fluoro-[2R-(butyroxylmethyl)-1,3-oxathiolan-5R-yl]-2(1H)-pyrimidinone Triethylamine (84.8 g, 0.84 mol), toluene (57 mL) and 4-(dimethylamino)pyridine (0.57 g) are combined and cooled to 0–5° C. 4-Amino-5-fluoro-[2R-(hydroxylmethyl)-1,3-oxathiolan-5R-yl]-2(1H)-pyrimidinone hydrochloride (56.8 g, 0.2 mol) is added in portions and the temperature rose from 5 to 10° C. during the addition. The mixture is cooled to 0 to 5° C. and butyric anhydride (75.9 g, 0.48 mol) is added at such a rate as to maintain 30 to 45° C. during the addition to give a thick white suspension. The suspension is stirred at 30 to 45° C. for 30 min, then heated to 40 to 50° C. and maintain at this temperature for 2–3 h. The most of solids dissolved and the reaction mixture becomes a light, pale yellow suspension. The progress of the reaction is monitored by TLC (heptane-ethyl acetate, 2:1) or $^1$H NMR. After the reaction is complete, it is diluted with toluene (224 mL) and cooled to 0–5° C. Water (224 mL) is added in portions while keeping the temperature below 20° C. The phases are separated, and the aqueous phase is extracted twice with toluene (2×112 mL). The combined toluene phases are washed with water (112 mL) to give a slightly yellow solution. The solution is vacuum concentrated to 165–170 mL and diluted with methylene chloride (57.0 mL). The resultant yellow/light brown solution (225 mL) containing the title compound is used directly in the next reaction (example 2).

EXAMPLE 2

Trans-glycosylation/anomerization

The 4-butyrylamino-5-fluoro-[2R-(butyroxylmethyl)-1,3-oxathiolan-5R-yl]-2(1H)-pyrimidinone solution (225 mL) from Example 1 is cooled to 0–5° C., and Iodotrimethylsilane (56.03 g, 0.28 mol) is added portionwise from an addition funnel while maintaining the reaction temperature below 20° C., and the addition funnel is rinsed with toluene (10 mL). The solution is cooled to 0–5° C., and maintained for 15–30 min. A solution of di-N,O-trimethylsily-5-fluorocytosine in toluene (205.8 g as solution. made from 18.07 g (0.14 mol) of 5-fluorocytosine with 1,1,1,3,3,3-hexamethyldisilazane in toluene) is added in portions while maintaining the temperature below 20° C. The mixture is allowed to warm to 20–25° C. on its own and maintained for 3–4 h. The cis-/trans-ratio is checked by $^1$H NMR of the reaction mixture and it is 1.0. The reaction mixture is diluted with ethyl acetate (284 mL) and cooled to 0–5° C. Saturated aqueous sodium bicarbonate (700 mL) is added to the reaction mixture in small portions while maintaining the temperature below 20° C. The pH of the aqueous is checked and adjusted to more than 7.0 if necessary with more saturated aqueous sodium bicarbonate. The mixture is filtered and the solids are washed with ethyl acetate (2×90 mL). The solids are 4-N-butyryl-5-fluorocytosine and can be potentially be recycled. The filtrate phases are separated, and the aqueous phase is extracted with ethyl acetate (2×170 mL). The combined organic phases are washed with water (2×224 mL). The yellow solution is vacuum concentrated to 200 mL to give a thick syrup containing white solids. Ethanol (200 mL) is added, and the mixture is concentrated to 150 mL. $^1$H NMR analysis is made for ethyl acetate content, and if it is greater than 10 mol % relative to FTC, more ethanol (150 mL) is added and vacuum concentrated to 150 mL again. The resultant mixture is ready for use for the next reaction (Example 3).

EXAMPLE 3

Cis-(−)-4-Amino-5-fluoro-[2-(hydroxylmethyl)-1,3-oxathiolan-5-yl]-2(1H)-pyrimidinone Mesylate and 4-Amino-5-fluoro-[2R-(hydroxylmethyl)-1,3-oxathiolan-5R-yl]-2(1H)-pyrimidinone Hydrochloride A solution (280 mL, prepared from 100 g (0.352 mol) of 4-amino-5-fluoro-[2R-(hydroxylmethyl)-1,3-oxathiolan- 5R-yl]-2(1H)-pyrimidinone hydrochloride as per procedure of Example 2) is diluted with methanol (500 mL) and cooled to 0–5° C. Aqueous ammonia solution (28 wt. %, 214 g, 3.52 mol) is added to the reaction mixture, and it is allowed to warm to 20–25° C. and maintained for 10 h. The progress of the reaction is monitored by TLC (ethyl acetate-Methanol, 9:1). After the reaction is complete, it is vacuum concentrated at 30–40° C. to 300 mL. The residue is diluted with n-butanol (500 mL), and vacuum concentrated to 300 mL. Methanol (600 mL) is added, and the solution is cooled to 0–5° C. Methanesulfonic acid (37.2 g, 0.387 mol) is added to the reaction mixture. The mixture is allowed to warm to 20–25° C., and concentrated to about 300 mL. Ethanol (450 mL) is added and the resulting suspension is concentrated to about 450 mL. The mixture is heated to 40° C., and ethyl acetate (450 mL) is added at this temperature in portions and the mixture is allowed to reflux for 0.5 hour. The suspension is slowly cooled to 20–25° C. and stirred for 15–18 hours. Further cooled to 0–5° C. for 2 hours, filtered, washed with ethyl acetate/ethanol (3:1) and dried on high vacuum at 40–45° C. to provide 50.17 g (41.5%) of cis-(−)-4-amino-5-fluoro-1-(2-(hydroxymethyl)-1,3-oxathiolan-5-yl)-2-(11H)-1-pyrimidinone mesylate. (96.3% purity by $^1$H NMR). The above filtrate is transferred into a 2 L, 3-necked flask equipped with a mechanical stirrer, a thermometer and a 10% aqueous sodium hydroxide trap. The flask is cooled to 0–5° C. and charged with 20% HCl in IPA (38.54 g, 0.21 mol) and stirred at 20–25° C. over a period of 15–18 hours. The suspension is concentrated to 440–450 mL and diluted with 450 ml of ethyl acetate. The suspension is cooled to 0–5° C. for 2–3 hours, filtered, washed with ethyl acetate/ethanol (3:1) and dried on high vacuum at 40–45° C. to provide 40.85 g (40.85%) of the 4-amino-5-fluoro-1-(2R-(hydroxymethyl)-1,3-oxathiolan-5R-yl)-2(1H)-1-pyrimidinone hydrochloride (97.3% purity by $^1$H NMR).

If necessary, cis-(−)-4-amino-5-fluoro-1-(2-(hydroxymethyl)-1,3-oxathiolan-5-yl)-2-(1H)-1-pyrimidinone mesylate can be repulped from an organic solvent or a solvent mixture, for instance, in 9–15 volumes of ethyl acetate/ethanol (2:1, v/v) to give the mesylate with >99% purity.

EXAMPLE 4 cis-(−)-4-Amino-5-fluoro-[2-(hydroxylmethyl)-1,3-oxathiolan-5-yl]-2(1H)-pyrimidinone (2, (−)-FTC)

Cis-(−)-4-Amino-5-fluoro-1-(2-(hydroxymethyl)-1,3-oxathiolan-5-yl)-2-(1H)-1-pyrimidinone mesylate (14.0 g, 0.0408 mol) is suspended in methanol (70 mL) and 28 wt % aqueous ammonia solution (2.97 g, 0.0488 mol) is added while keeping the temperature below 25° C. to give a clear colorless solution. The mixture is stirred at 20–25° C. for 30 min. Ethyl acetate (280 mL) is added, and during which time white precipitate formed and the mixture is stirred for 30 min. The suspensions is filtered through a Celite pad and washed with ethyl acetate/methanol (4:1, v/v) (2×28 mL). To the solution is added triethylamine (0.43 g) and it is vacuum concentrated at 30–40° C. to about 200 mL. Ethanol (40 mL) is added and vacuum concentrated at 30–40° C. to 55–60 mL to give a white suspension. Small sample is taken for 1H NMR analysis for the ethyl acetate/ethanol ratio which should be 3–5 (v/v) and, if not, it is adjusted appropriately. Triethylamine (0.43 g) is added, and the mixture is heated to reflux and maintain refluxing for 30 min. The mixture is cooled to 20–25° C., maintained for 1–2 h, cooled to 0–5° C. and maintained for another 1–2 h. Filtered and washed with ethyl acetate/ethanol (3:1, v/v) (2×20 mL). The solids are vacuum dried at 40–50° C. for 3 h to give 8.54 g (85%) of pure cis-(−)-4-amino-5-fluoro-[2-(hydroxylmethyl)-1,3-oxathiolan-5-yl]-2(1H)-pyrimidinone (2, (−)-FTC).

The mother liquor is cooled to 0–5° C. and methanesulfonic acid (0.9 g) is added. The mixture is vacuum concentrated at 30–40° C. to 15–20 mL, ethyl acetate (20 mL) is added. The resultant white suspension is refluxed for 15 min, cooled to 0–5° C. and maintained for 1 h. The mixture is filtered, and washed with ethyl acetate/ethanol (2:1, v/v) (2×5 mL) and vacuum dried at 20–25° C. for 4 h to give 1.8 g (12.9%) of cis-(−)-4-amino-5-fluoro-1-(2-(hydroxymethyl)-1,3-oxathiolan-5-yl)-2-(1H)-1-pyrimidinone mesylate.

EXAMPLE 5

Cis-(−)-4-Amino-5-fluoro-[2-(hydroxylmethyl)-1,3-oxathiolan-5-yl]-2(1H)-pyrimidinone Hydrochloride and 4-Amino-5-fluoro-[2R-(hydroxylmethyl)-1,3-oxathiolan-5R-yl]-2(1H)-pyrimidinone Hydrochloride To a 1 L round bottom flask, fitted with a magnetic stirrer and a condenser, are added cis-/trans-(−)-4-amino-5-fluoro-1-(2-(hydroxymethyl)-1,3-oxathiolan-5-yl)-2(1H)-pyrimidinone HCl salt (25.7 g, cis-(−)-FTC: 49.61%; trans-(−)-FTC: 45.25%) and industrial ethanol (590 mL). The suspension is stirred at 40° C. for 3 hours, then filtered at this temperature and the solid cake is washed with industrial ethanol (3×25 mL). The solid is dried in vacuum to give a white solid (8.3 g, cis-(−)-FTC: 1.9%; trans-(−)-FTC: 96.3%). The filtrate (HPLC: cis-(−)/trans-(−)=3.72:1) is concentrated at 80° C. with slightly vacuum to 170 mL. Cis-(−)-FTC HCl salt crystals are added as seeds at this temperature, and the solution is allowed to cool slowly to room temperature without stirring. Upon being kept at room temperature for 18 hours, the mixture is filtered, and the solid cake is washed with ethanol (denatured with 0.5% toluene) (3×15 mL). The solid is dried in vacuum to give white crystals (10.08 g, 79% yield. HPLC assay: cis-(−)-FTC: 96.9%; trans-(−)-FTC: 3.1%.). The mother liquid (cis/trans=1:1.12) can be recycled.

If necessary, cis-(−)-4-amino-5-fluoro-1-(2-(hydroxymethyl)-1,3-oxathiolan-5-yl)-2-(1H)-1-pyrimidinone hydrochloride can be repulped from an organic solvent or a solvent mixture, for instance, in ethanol or ethanol/methanol mixture to give the hydrochloride with >99% purity.

EXAMPLE 6 cis-(−)-4-Amino-5-fluoro-1-(2-(hydroxymethyl)-1,3-oxathiolan-5-yl)-2-(1H)-1-pyrimidinone (2, (−)-FTC)

To a 250 mL round bottom flask, fitted with a magnetic stirrer, are added cis-(−)-4-amino-5-fluoro-1-(2-(hydroxymethyl)-1,3-oxathiolan-5-yl)-2(1H)-pyrimidinone HCl salt (5 g, 17.63 mmol, 99.4% purity) and methanol (25 mL). The mixture is stirred at room temperature, and to it is added $Na_2CO_3$ solid (1.12 g, 10.6 mmol). $CO_2$ gas comes out immediately after the addition. Upon being stirred at room temperature for 3 hours, the reaction mixture is diluted with ethyl acetate (125 mL) and stirred at room temperature for 1 hour. Then the mixture is filtered through a silica gel-Celite pad, and the pad is washed with ethyl acetate-methanol (5:1, v/v) (20 mL). The filtrate is concentrated at 40–50° C. to 20 mL, and to it is added ethanol (5 mL). The resulting mixture is stirred at 60° C. for 15 minutes, then cooled to 0° C. and stirred at 0° C. for 1.5 hours. The mixture is filtered and the solid cake is washed with ethyl acetate. The solid is dried in vacuum at 45° C. for 12 hours to afford (−)-FTC as white solids (3.7 g, 86%, HPLC assay: 99.7% purity). The mother liquid is concentrated to 5 mL, and stirred at room temperature. Filtration gave (−)-FTC as white crystals (0.2 g, 4.7%).

While the foregoing provides a detailed description of a preferred embodiment of the invention, it is to be understood that this description is illustrative only of the principles of the invention and not limitative. Furthermore, as many changes can be made to the invention without departing from the scope of the invention, it is intended that all material contained herein be interpreted as illustrative of the invention and not in a limiting sense.

The embodiments of the invention in which an exclusive property or privilege is claimed are as follow:

1. Cis-(−)-4-amino-1-[2-(hydroxymethyl)-1,3-oxathiolan-5-yl]2(1H)-pyrimidinone, mesylate.

2. Cis-(−)-4-amino-5-fluoro-1-[2-(hydroxymethyl)-1,3-oxathiolan-5-yl]-2(1H)-pyrimidinone, mesylate.

3. A process for the preparation of 1,3-oxathiolane nucleoside analogues in predominantly the cis-form, from mixture of cis-/trans-1,3-oxathiolane nucleosides or their protected derivatives thereof, comprising:

(i) treatment of the cis-/trans-1,3-oxathiolane nucleosides (or protected derivatives thereof) with a pyrimidine base (or pyrimidine base derivatives thereof) and an acid, (ii) adding a suitable acid to the obtained cis-/trans-mixture of isomers, (iii) selective crystallization of the desired cis-isomer salt from a solvent or combination of solvents, and (iv) treatment of the predominantly cis-isomer salt with a suitable base to offer the free 1,3-oxathiolane nucleosides, and thereafter optionally repeating steps (i) to (iv) inclusive.

4. The process of claim 3 wherein the 1,3-oxathiolane nucleoside produced is cis-(−)-4-amino-1-[2-(hydroxymethyl)-1,3-oxathiolan-5-yl]-2(1H)-pyrimidinone (Lamivudine, 3TC).

5. The process of claim 3 wherein the 1,3-oxathiolane nucleoside produced is cis-(−)-4-amino-5-fluoro-1-[2-(hydroxymethyl)-1,3-oxathiolan-5-yl]-2(1H)-pyrimidinone (Emtricitabine, (−)-FTC).

6. The process of claim 3, 4 or 5 wherein the pyrimidine base is N,O-disilyled cytosine.

7. The process of claim 3, 4 or 5 wherein the pyrimidine base is N,O-disilyled 5-fluoro-cytosine.

8. The process of claim 3, 4 or 5 wherein the acid for anomerization/trans-glycosylation is iodotrimethylsilane or trimethylsilyl trifluoromethanesulfonate.

9. The process of claim 3, 4 or 5 wherein the acid used for salt formation is methanesulfonic acid or hydrochloric acid.

10. The process of claim 3, 4 or 5 wherein the solvent for crystallization is ethanol, methanol, and ethyl acetate.

11. A process comprising treating a mixture of cis-/trans-isomers of 1,3-oxathiolane nucleoside analogues (6)

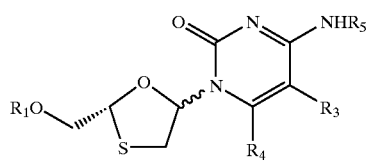

cis-/trans-isomer mixture with inorganic or organic acids in a single solvent or solvent mixture; the corresponding salts of the isomers being thereafter separated in high optical purity by fractional crystallization, the desired cis-nucleoside salts (7)

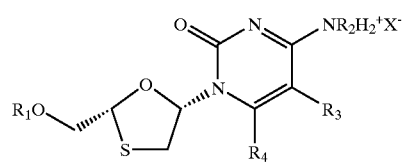

cis-isomer salt being isolated and converted into their corresponding free base form (9) by treatment with organic or inorganic bases in a single solvent or a solvent mixture, the undesired trans-nucleoside salts (8)

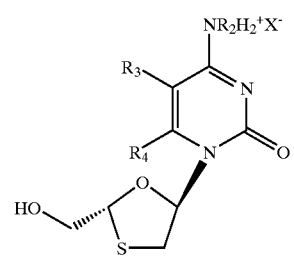

trans-isomer
salt
Can be recycled also being isolated and recycled by repeating the process thereby to produce

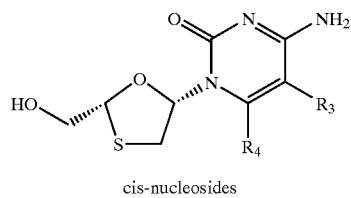

cis-nucleosides $$\begin{bmatrix} 1.\ R_3=R_4=H,\ 3TC \\ 2.\ R_3=F, R_4=H,\ FTC \end{bmatrix}$$

wherein $R_1$ is selected from hydrogen, low alkyl, aryl, alkylsilyl, and acyl groups, $R_2$ selected from hydrogen, alkyl, aryl, and alkylsilyl acyl groups and $R_3$ and $R_4$ are independently selected from the group consisting of hydrogen, bromine, chlorine, fluorine, iodine, low alkyl, aryl, amino and hydroxyl groups.

12. The process of claim 11 wherein $R_3=R_4=H$ and the compound is 3TC.

13. The process of claim 11 wherein $R_3$ is F, $R_4$ is H and the compound is FTC.

14. The process of claim 11 wherein the inorganic and organic acids are selected from methanesulfonic acid, hydrochloric acid, hydrobromic acid, sulfuric acid, benzenesulfonic acid, p-toluenesulfonic acid.

15. The process of claim 11 wherein the acid is selected from methanesulfonic acid, hydrochloric acid, and the like.

16. The process of claim 11, 14 or 15 wherein the amount of the acid can range from 0.5 to 5 moles per mole of the nucleoside.

17. The process of claim 11, 14 or 15 wherein the amount of the acid is from 1.0 mole to 1.5 moles per mole of the nucleoside.

* * * * *